United States Patent

Musco et al.

[11] 4,167,513
[45] Sep. 11, 1979

[54] SYNTHESIS OF UNSATURATED ESTERS AND LACTONE FROM BUTADIENE AND CARBON DIOXIDE

[75] Inventors: Alfredo Musco, Segrate; Roberto Santi; Gian P. Chiusoli, both of Novara, all of Italy

[73] Assignee: Montedison S.p.A., Milan, Italy

[21] Appl. No.: 939,793

[22] Filed: Sep. 5, 1978

[30] Foreign Application Priority Data

Sep. 6, 1977 [IT] Italy .................. 27277 A/77

[51] Int. Cl.² .................. C07D 309/30; C07C 69/61
[52] U.S. Cl. .................. 260/343.5; 560/225
[58] Field of Search .................. 260/343.5; 560/225

[56] References Cited

U.S. PATENT DOCUMENTS 3,701,787  10/1972  Evans et al. .................. 260/343.5
3,743,657  7/1973  Watanabe et al. .................. 560/225

OTHER PUBLICATIONS

Sasaki et al., *J.C.S. Chem. Comm.*, 1976, pp. 605–606.

*Primary Examiner*—Alan L. Rotman
*Assistant Examiner*—Robert C. Whittenbaugh

*Attorney, Agent, or Firm*—Stevens, Davis, Miller & Mosher

[57] ABSTRACT

Octadienyl esters of 2-ethylidene-hepta-3,5-dienoic and 2-vinyl-hepta-3,5-dienoic acids of formula $C_8H_{11}COOC_8H_{13}$ and δ-lactone of formula

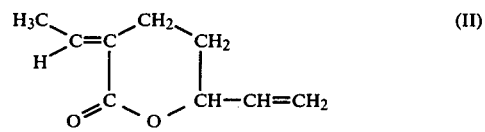

or 2-ethylidene-hepta-6-ene-5-olide, are prepared by reaction of 1,3-butadiene with $CO_2$ at a temperature comprised between about 20° and 150° C. and at a total pressure between about 10 and 500 atm in the presence of a phosphinic complex of palladium having the formula $Pd[P(R)_3]_x$, wherein x is an integer from 2 to 4, and $(R)_3$ is a homogeneous or heterogeneous group consisting of alkyls, cycloalkyls having up to 8 carbon atoms and of phenyls, also substituted, in an inert atmosphere.

The obtained products are "per se" new and are valuable intermediates for synthesis of chemicals (fungicides, pesticides, etc.) and in particular as effective plasticizers.

2 Claims, No Drawings

SYNTHESIS OF UNSATURATED ESTERS AND LACTONE FROM BUTADIENE AND CARBON DIOXIDE

This invention relates to a process for preparing unsaturated esters from butadiene and carbon dioxide.

In particular, the present invention relates to a process for preparing unsaturated esters of nonatrienoic acids by carboxylation of butadiene.

More in particular this invention relates to a catalytic process for preparing the octadienyl ester of 2-ethylidene, hepta-3,5-dienoic acid and 2-vinyl-hepta-3,5-dienoic acid, having the empirical formula $C_8H_{11}COOC_8H_{13}$ (I), and isomers thereof by catalytic synthesis from butadiene and carbon dioxide.

The esters are obtained in the various possible isomeric forms and mixtures thereof. Finally, according to a further feature of the present invention, whereto we purpose to extend the scope of protection of this invention, besides esters (I) it is possible to obtain also the lactone, structurally an "inside" ester, having the formula (II):

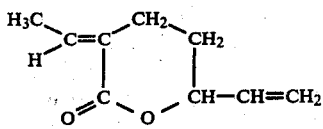

(II)

or 2-ethylidene-hepta-6-ene-5-olide.

The octadienyl isomeric esters of the nonatrienoic acids (I) and lactone (II) obtained as such are compounds not described in themselves, whereto we intend to extend the scope of the present invention.

The compounds obtained are interesting products having important applicative possibilities in the industry. In fact they can be utilized, besides as valuable intermediates for organic syntheses in general, and in particular in the field of the fine chemistry for the synthesis of fungicides, pesticides, etc., also for preparing effective plasticizers for plastic materials such as PVC, polystyrene, etc., by hydrogenation of the unsaturated esters and lactone to the corresponding saturated esters and saturated lactone, etc.

It is known how to prepare nonatrienoic isomeric acids also in the form of lactones by carboxylation of butadiene with gaseous $CO_2$ conducted in dipolar aprotic solvents in the presence of catalysts composed of phosphinic complexes of palladium, having a chelating structure, such as, for example $Pd[Ph_2P(CH_2)_2PPh_2]_2$. The abovesaid technique, however, is limited to the preparation of the acids and/or of $\gamma$-lactones, while no mention is made of the presence of esters.

Nevertheless such technique is questionable in the economical-industrial respect due to the low yields disclosed and to the necessity of using special solvents, such as dimethyl-formamide, dimethyl-sulphoxide etc., as well as to the difficult and expensive procurement or preparation of the catalyst based on a phosphinic complex of palladium having a chelating function.

Furthermore, in respect of the aforesaid prior art, the present invention represents an unexpectable overcoming of a prejudice existing in the art itself.

The art, in fact, considers as preparable, by reaction of butadiene with $CO_2$, only the acid, in the isomeric form, and/or the $\gamma$-lactone thereof, wherefore this teaching per se should have deterred those skilled in the art from further researches on such reaction with a view of obtaining the esters and the $\gamma$-lactone of the present invention.

Thus it is an object of this invention to provide a simple and economic method of preparing octadienyl esters of nonatrienoic acids (I) and the $\gamma$-lactone of formula (II), free from the drawbacks of the art.

Another object is to provide new compounds having useful industrial applications.

These and still other objects, that will more clearly appear to those skilled in the art from the following description, are achieved, according to the present invention, by the octadienyl isomeric esters of the nonatrienoic acids of formula (I) and the $\gamma$-lactone of formula (II), and by the process for preparing same, which is characterized in that 1,3-butadiene is reacted with $CO_2$ at a temperature comprised between about 20° and 150° C. and at a total pressure between about 10 and 500 atm in the presence of a phosphinic complex of palladium having the formula $Pd[P(R)_3]_x$, wherein x is an integer from 2 to 4, and $(R)_3$ is a homogeneous or heterogeneous group consisting of alkyls, cycloalkyls having up to 8 carbon atoms and of phenyls, also substituted, in an inert atmosphere.

For the esters of formula (I) the reaction can be schematically represented by the following equation:

The raw reaction mixture is composed, besides by lesser amounts of acids, by $\gamma$-lactone (II), by esters (I) and isomers thereof.

In other terms: in this manner it is possible to obtain the octadienyl esters of nonatrienoic acids (I) also in the form of mixture of their possible isomers, and the $\delta$-lactone of formula (II).

As already told above, the reaction is conducted also in the absence of solvents, though the use of solvents is compatible and these are selected from the aromatic hydrocarbons (benzene, toluene, etc.) and the esters (tetrahydrofuran, etc.).

The total pressure preferably ranges from 50 to 200 atm and the temperature from about 50° to 100° C. to obtain prevailingly esters (I), while for obtaining prevailingly the $\gamma$-lactone (II) the total pressure ranges from 250 to 300 atm and the preferred temperature from 60° to 85° C. Reaction times of from 3 to 24 hours and above are sufficient for the conclusion of the reaction. The reaction is conducted in an inert gaseous atmosphere consisting, for example, of nitrogen, $CO_2$, argon etc.

In the event it is operated in a solution, the concentration thereof is not discriminant for the purpose of a correct execution of the process, however it will be useful to bear in mind that it is possible to operate with values of the reagents' concentration up to above 50% by weight.

The reaction is finally conducted in the presence of a complex palladium catalyst of formula $Pd[P(R)_3]_x$, in which symbols x and R have the above meaning.

It is possible to employ mixtures of the aforesaid palladium complexes.

It is to be noticed that the catalysts utilized according to the present invention, contrary to what described in the previously discussed prior art, do not possess in their structure any possibility of carrying out a chelating action.

The phosphine complexes utilized as catalysts are known compounds easy to be found on the market, which in any case can be prepared according to known techniques, for example by reaction of $PdCl_2(C_6H_5CN)_2$ and phosphine in the presence of reducing agents.

The complex palladium catalyst can be also directly prepared in the reaction medium "in situ", in the presence of butadiene, starting from compounds which are precursors of the complex, i.e. from compounds that in the reaction environment lead to the formation of the desired palladium complex.

For example, instead of the palladium complex it is possible to introduce into the reactor an organic salt of palladium such as the acetate, propionate, acetylacetonate, and the above-defined phosphine $P(R)_3$, according to conventional techniques.

Palladium triethylphosphine, palladium tributylphosphine, palladium tricyclohexylphosphine and palladium triphenylphosphine have proved to be effective phosphinic complexes of palladium.

The reacting substances are employed in ratios that can vary over a wide range. Advantageous results are achieved by using 1 to 10 moles of $CO_2$ for 1 mole of butadiene, preferably 2 to 6 moles of $CO_2$ for 1 mole of butadiene.

Likewise 0.1 to 0.001 moles of complex palladium catalyst for 1 mole of butadiene, preferably 0.01 to 0.002 moles for 1 mole, are employed.

In the event that the complex catalyst is prepared "in situ", 2 to 4 moles of phosphine $P(R)_3$ for 1 mole of palladium salt, preferably about 3 moles, are usually employed.

At the conclusion of the reaction the raw reaction mixture contains, as specified hereinbefore, besides the octadienyl esters of nonatrienoic acids (I) and the γ-lactone (II), in their isomeric forms, smaller amounts of butadiene oligomers and of free acid as by-products and isomers thereof, besides small amounts of the butenyl esters of the nonatrienoic acids.

The γ-lactone (II) is quantitatively obtainable, if desired according to the same reaction of this invention, by suitably selecting the catalysts and the parameters in the ranges of pressure, temperature and times, as indicated hereinbefore.

In fact, the above-said process for preparing the esters (I) and/or the unsaturated γ-lactone (II) results to be extremely sensible to the operative conditions selected (catalyst, pressure, temperature, etc.); depending on such conditions, the final reaction mixture consists of various products in a quantitative ratio variable just as a function of the existing chosen conditions.

The resulting esters (I) and the γ-lactone (II) are separated from the raw reaction mixture according to substantially conventional methods; for example by distillation of the utilized solvent, if any, and of the existing butadiene oligomers, and by successive removal of the catalyst in a silica column, using a mixture of cyclohexane and ethyl-acetate etc. as eluting agent.

In a practical embodiment the process is conducted as follows.

The solvent, if any, the palladium phosphinic complex compound or the organic salt and the phosphine are introduced into a reactor equipped with thermoregulating and reagent feeding systems, after having blown off the air by means of vacuum and of an inert gas (nitrogen). Butadiene is then added. Subsequently $CO_2$ is introduced up to the total pressure or to a pre- fixed amount, and the whole is brought to the desired reaction temperature. At the conclusion of the reaction the volatile fractions are distilled, it is filtered on an acid $SiO_2$ layer and it is washed with cyclohexane and ethyl-acetate. After evaporation of the ethyl-acetate and of the cyclohexane, a mixture of the isomeric esters (I) of formula $C_8H_{11}COOC_8H_{13}$ and of the γ-lactone (II) is obtained, such products being separable by means of conventional techniques (chromatography, etc.).

Thanks to the mild operative conditions and to the high selectivity of the catalysts, the process appears particularly efficient.

A further advantage consists in the possibility of using butadiene also in the presence of other olefins. By consequence it is possible to directly employ fraction $C_4$ of industrial petroleum cuts containing butadiene in admixture with other olefins.

The present invention will be now further described in the following examples, which are given however for illustrative purposes; example 6 is given by way of comparison and utilizes the complexes of Pd with phosphines having a chelating structure according to the art; example 10 shows an application of the esters of this invention as plasticizing agents.

EXAMPLE 1

24 ml of butadiene (17 g, 0.31 moles), 0.36 g (0.78 m moles) of $Pd[P(C_2H_5)_3]_2$, (butadiene:Pd molar ratio=400:1), 36 g of $CO_2$ ($CO_2$:butadiene molar ratio=2.6:1) were introduced into a 75 ml autoclave. It was heated 17 hours to 80° C.

A pressure of 205 atm was reached. It was cooled to room temperature, $CO_2$ and the volatile fraction were stripped at $10^{-3}$ mm/Hg, at room temperature. The distillate (8.3 g) prevailingly consisted of octatrienes.

The residue (6.0 g) predominantly consisted of the isomers of ester (I): $C_8H_{11}COOC_8H_{13}$, that was identified as follows. The raw residue was eluted on a $SiO_2$ column, using as eluent a mixture of cyclohexane (98%) and of ethyl-acetate (2%). 0.6 g of residue, obtained by evaporation of the solvent from the first fractions containing esters (I), were hydrogenated with $PdCl_2$ (60 mg), reduced by $NaBH_4$ (30 mg), in cyclohexane at 60 atm of $H_2$ at 55° C.

The cyclohexane solution, after filtering of the catalyst, was evaporated, thus giving 0.55 g of residue.

The residue, after washing with $NaHCO_3$ to remove small amounts of 2-ethyl-heptanoic acid, was characterized as a mixture of 2-ethyl-heptanoate of 1-octyl and of 2-ethyl-heptanoate of 3-octyl by means of mass spectography, I.R. and N.M.R. analyses, that confirmed that the abovesaid structure.

Further 0.31 g of the residue consisting of ester (I) were treated with 3 ml of 10% NaOH and with 10 ml of methanol at room temperature for 8 hours. The methanol solution was diluted with water and extracted with ether. The ether solution contained 0.14 g of 2,7-octadien-1-ol and 1,7-octadien-3-ol in a ratio by weight of about 2:1. The aqueous solution, acidified with $H_2SO_4$ at 10% and extracted with ether, after evaporation of ether gave 0.14 g of 2-ethylidene-hepta-3,5-dienoic acid (cis:trans ratio=1:2). The mass spectrography as well as the N.M.R. and I.R. analyses confirmed the expected structure.

The successive fractions predominantly contained the unsaturated δ-lactone (II).

EXAMPLE 2

32 ml (22.6 g, 0.41 moles) of butadiene, 0.5 g (1.08 m moles) of Pd[P($C_2H_5$)$_3$]$_3$ (butadiene:Pd molar ratio=380:1), and $CO_2$ up to a pressure of 50 atm at 25° C. were introduced into a 200 ml autoclave. It was heated to 80° C. for 24 hours.

The pressure rose up to a maximum value of 100 atm. The reaction mixture, cooled down to room temperature, was stripped from the volatile fraction at $10^{-3}$ mm/Hg. 18 cc of butadiene dimers and 8.3 g of residue were obtained. The residue was mainly made up of ester (I) and of 1.3 g of the corresponding unsaturated acid. The ester was characterized according to the methods described in example 1.

EXAMPLE 3

0.53 g (0.8 m moles) of Pd[P(cyclo-$C_6H_{11}$)$_3$]$_2$ in 10 ml of benzene, 24 ml (16.9 g, 0.31 moles) of butadiene (butadiene:Pd molar ratio=390:1), 39 g (0.88 moles) of $CO_2$ ($CO_2$:butadiene molar ratio=2.85:1) were introduced into a 75 ml autoclave.

It was heated to 80°–85° C. for 17 hours and a maximum pressure of 300 atm was reached. After cooling and stripping at $10^{-3}$ mm/Hg at 25° C., 9.5 g of residue were obtained. The distillate essentially consisted of the butadiene dimers, the residue was mainly made up of the δ-lactone (II) and of about 20% of the ester (I) and isomers thereof. The lactone was determined according to conventional methods.

EXAMPLE 4

5 cc of tetrahydrofuran (THF), 0.35 g (1.56 m moles) of Pd acetate, Pd($OCOCH_3$)$_2$, 0.81 g (3.12 m moles) of triphenylphosphine were introduced, in an argon flow, into a glass phial suitable for an oscillating 1-liter autoclave. The phial was placed into a cold bath, whereupon 25 g (0.46 moles) of butadiene were introduced by distillation into the phial. The whole was placed into the autoclave, it was pressurized to 50 atm with $CO_2$ and it was heated to 50° C. for 6 hours. After stripping at 0.1 mm/Hg at 25° C. for 2 hours and elimination of the catalyst on $SiO_2$ as in example 1, 8.2 g of residue were obtained, that, after hydrogenation on Pd, chiefly consisted of the 1- and 3-octyl esters of 2-ethyl-heptanoic acid.

EXAMPLE 5

Following the modalities of example 4, 0.35 g (1.56 m moles) of Pd($OCOCH_3$)$_2$, 0.36 g (3.12 m moles) of P($C_2H_5$)$_3$ and 25 g (0.46 moles) of butadiene and $CO_2$ (50 atm) were reacted in 5 cc of THF. 6.3 g of a residue having the same characteristics as the residue of example 4 were obtained.

EXAMPLE 6 (COMPARATIVE EXAMPLE)

Following the modalities of example 4, 0.35 g (1.56 m moles) of Pd($OCOCH_3$)$_2$, 0.62 g (1.56 m moles) of ($C_6H_5$)$_2$P($CH_2$)$_2$P($C_6H_5$)$_2$ and 25 g (0.46 moles) of butadiene and $CO_2$ (50 atm) were reacted in 5 cc of THF.

After stripping and removal of the catalyst on $SiO_2$ as in example 1, 1.8 g of a residue having characteristics similar to that of example 4 were obtained. It is evident, in respect of example 4, that the use of the phosphines having a chelating structure according to the present comparative example lead to lower yields.

EXAMPLE 7

The reaction was conducted as in example 4 and using 1.62 g (6.24 m moles) of P($C_6H_5$)$_3$ (P/Pd=4). After stripping, 9.0 g of a residue having for the most part the characteristics of the residue of example 4 were obtained.

EXAMPLE 8

The reaction was conducted according to the modalities of example 4 and the temperature was kept at 80° C. for 6 hours. 8.3 g of a residue containing after hydrogenation chiefly octyl esters of 2-ethyl-heptanoic acid were obtained after stripping.

EXAMPLE 9

The reaction was conducted as in example 4. Instead of pure butadiene, use was made of 25 g of fraction $C_4$ coming from petroleum cuts and exhibiting, on gas-chromatographic analysis, a molar distribution of the main products in the following order: butadiene: 40%, 1-butene: 26%, n-butane: 16%, isobutene: 6%, trans-butene: 7%, vinyl-cyclohexane: 3%.

After stripping and purification of the residue from the catalyst through filtering on $SiO_2$, 4.22 g of a product consisting for the most part of esters (I) were obtained.

EXAMPLE 10 (APPLICATIVE EXAMPLE)

12 g of ester (I) were hydrogenated according to the modalities of example 1 employing $PdCl_2$ (600 mg) and $NaBH_4$ (300 mg). After filtering and washing with $NaHCO_3$, 10.8 g of a mixture of saturated isomeric esters were obtained. The mixture so obtained was hydrogenated 3 hours at 225° C. and 300 atm of hydrogen in the presence of barium oxide and copper chromite (hydrogenolysis). By distillation of the reaction mixture at 92° C. and 5 mm/Hg, 4.5 g of 2-ethyl-1-heptanol were finally obtained. 4.5 g (0.031 moles) of 2-ethyl-1-heptanol containing a few drops of concentrated sulphuric acid and 2.2 g (0.015 moles) of phthalic anhydride were made to react in toluene, azeotropically distilling the reaction water. After washing first with sodium carbonate at 10% and successively with water, and drying under vacuum, 7.2 g of bis-2-ethylheptyl-phthalate were obtained. 100 parts of a PVC in powder, prepared according to the process in suspension and having the following basic characteristics:

K of Fitkeuscher=63±1
glass transition temperature=75°±1° C.
were additioned with 20 parts of bis-2-ethylheptyl-phthalate obtained as described hereinabove, and, as thermal stabilizers, with 3 parts of cadmium stearate and 1 part of alkyl-arylphosphite. It was homogenized in a two-roller open mixer at a temperature of 170°±5° C. for 5 minutes. After this treatment, the mixture was compression molded to 1-mm thick foils under the following conditions:

temperature of the plates: 190°±5° C.
pressure: 100 kg/cm²
molding time: 5 minutes
cooling rate in the press: 10° C./min.

From said foils, by hollow punching at room temperature, specimens were obtained which, after a 24 hours conditioning at 23° C. at 60% of relative humidity, were subjected to the tensile strength test according to standard ASTM D 638. The following results were obtained:

elastic modulus: 19,000±500 kg/cm$^2$
tensile stress: 400±20 kg/cm$^2$
elongation at break: 130±30%.
Conversely, on non-plasticized PVC specimens, prepared under the same conditions, the following values were determined:
elastic modulus: 30,000±1,000 kg/cm$^2$
tensile stress: 590±20 kg/cm$^2$
elongation at break: 8±2%,
which proved the good plasticizing characteristics of the product.

What we claim is:

1. As products new in themselves, the isomeric octadienyl esters of 2-ethylidenehepta-3,5-dienoic and 2-vinyl-hepta-3,5-dienoic acids of formula $C_8H_{11}COOC_8H_{13}$.

2. As a product new in itself, the unsaturated δ-lactone of formula (II):

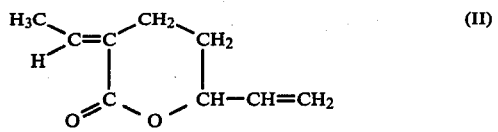

or 2-ethylidene-hepta-6-ene-5-olide.